US010065251B2

(12) United States Patent
Tortorella

(10) Patent No.: US 10,065,251 B2
(45) Date of Patent: Sep. 4, 2018

(54) CUTTING TOOLS FOR SAMPLE PREPARATION

(71) Applicant: GE Healthcare UK Limited, Little Chalfont (GB)

(72) Inventor: Stevan Paul Tortorella, Wells, ME (US)

(73) Assignee: GE HEALTHCARE UK LIMITED, Little Chalfont (GB)

(*) Notice: Subject to any disclaimer, the term of this patent is extended or adjusted under 35 U.S.C. 154(b) by 181 days.

(21) Appl. No.: 14/424,490

(22) PCT Filed: Aug. 29, 2013

(86) PCT No.: PCT/EP2013/067869
§ 371 (c)(1),
(2) Date: Feb. 27, 2015

(87) PCT Pub. No.: WO2014/033200
PCT Pub. Date: Mar. 6, 2014

(65) Prior Publication Data
US 2015/0224669 A1  Aug. 13, 2015

(30) Foreign Application Priority Data
Aug. 31, 2012 (GB) .................................. 1215504.0

(51) Int. Cl.
*B23B 51/04* (2006.01)
*B23B 51/05* (2006.01)
(Continued)

(52) U.S. Cl.
CPC .... *B23B 51/0453* (2013.01); *A61B 17/32053* (2013.01); *B23B 51/05* (2013.01);
(Continued)

(58) Field of Classification Search
CPC ....... B23B 51/0453; B23B 51/05; B26F 1/32; A61B 17/32053; Y10T 408/51
See application file for complete search history.

(56) References Cited

U.S. PATENT DOCUMENTS 2,414,133 A * 1/1947 Barr ...................... E21B 25/005
                                                    408/145
2,987,922 A    6/1961 Harrington
(Continued)

FOREIGN PATENT DOCUMENTS

CA      2 380 736 A1    10/2003
DE         9206629 U1 *  9/1993 ......... B23B 51/0453
(Continued)

OTHER PUBLICATIONS

PCT International Search Report for PCT Application No. PCT/EP2013/067869 dated Nov. 19, 2013 (4 pages).
(Continued)

*Primary Examiner* — Eric A Gates
(74) *Attorney, Agent, or Firm* — Eversheds Sutherland (US) LLP

(57) ABSTRACT

A cutting tool is shown for cutting, handling and then ejecting disks of material cut from a sheet or like material, the tool comprising: a body having a proximal end adapted to be rotatably driven about an axis, and having a distal end including a generally cylindrical cutting portion rotatable about said axis for cutting and receiving said disks; an ejector slideable parallel with the axis and within said cylindrical cutting portion for ejecting the received cut disks; and a grip rotatably mounted to the body such that the grip can be held without substantial rotation while the body is rotated said grip being operable to cause said sliding of the ejector and for ejecting the disks.

14 Claims, 2 Drawing Sheets

Figure 2A:
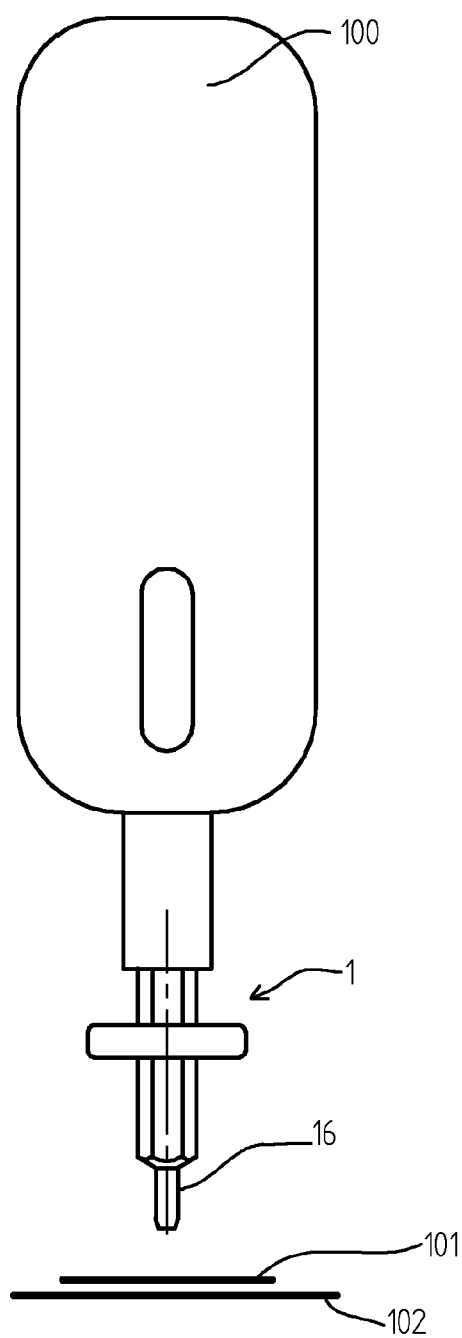

(51) Int. Cl.
  *B26F 1/32* (2006.01)
  *A61B 17/3205* (2006.01)
  *G01N 1/28* (2006.01)

(52) U.S. Cl.
  CPC ............... *B26F 1/32* (2013.01); *G01N 1/286* (2013.01); *G01N 2001/288* (2013.01); *Y10T 83/04* (2015.04); *Y10T 408/51* (2015.01)

(56) References Cited

U.S. PATENT DOCUMENTS

| | | | | |
|---|---|---|---|---|
| 4,234,375 A | * | 11/1980 | Ciccarello | A63B 45/02 |
| | | | | 156/475 |
| 4,406,334 A | * | 9/1983 | Baumann | B23B 51/042 |
| | | | | 175/315 |
| 4,738,255 A | | 4/1988 | Goble et al. | |
| 4,936,313 A | | 6/1990 | Burkhardt et al. | |
| 6,341,925 B1 | * | 1/2002 | Despres | B23B 51/0453 |
| | | | | 408/204 |
| 6,502,491 B2 | * | 1/2003 | Borowczak | B26D 7/1818 |
| | | | | 30/362 |
| 2005/0066751 A1 | | 3/2005 | Harris, II | |

FOREIGN PATENT DOCUMENTS

| | | | | |
|---|---|---|---|---|
| FR | 1590234 A | * | 4/1970 | ........... B23B 47/281 |
| WO | 84/01827 A1 | | 5/1984 | |
| WO | 00/57153 A1 | | 9/2000 | |
| WO | 2011/134040 A1 | | 11/2011 | |

OTHER PUBLICATIONS

PCT Written Opinion for PCT Application No. PCT/EP/2013/067869 dated Nov. 19, 2013 (4 pages).
GB Search Report for GB Application No. 1215504.0 dated Dec. 13, 2012 (3 pages).

* cited by examiner

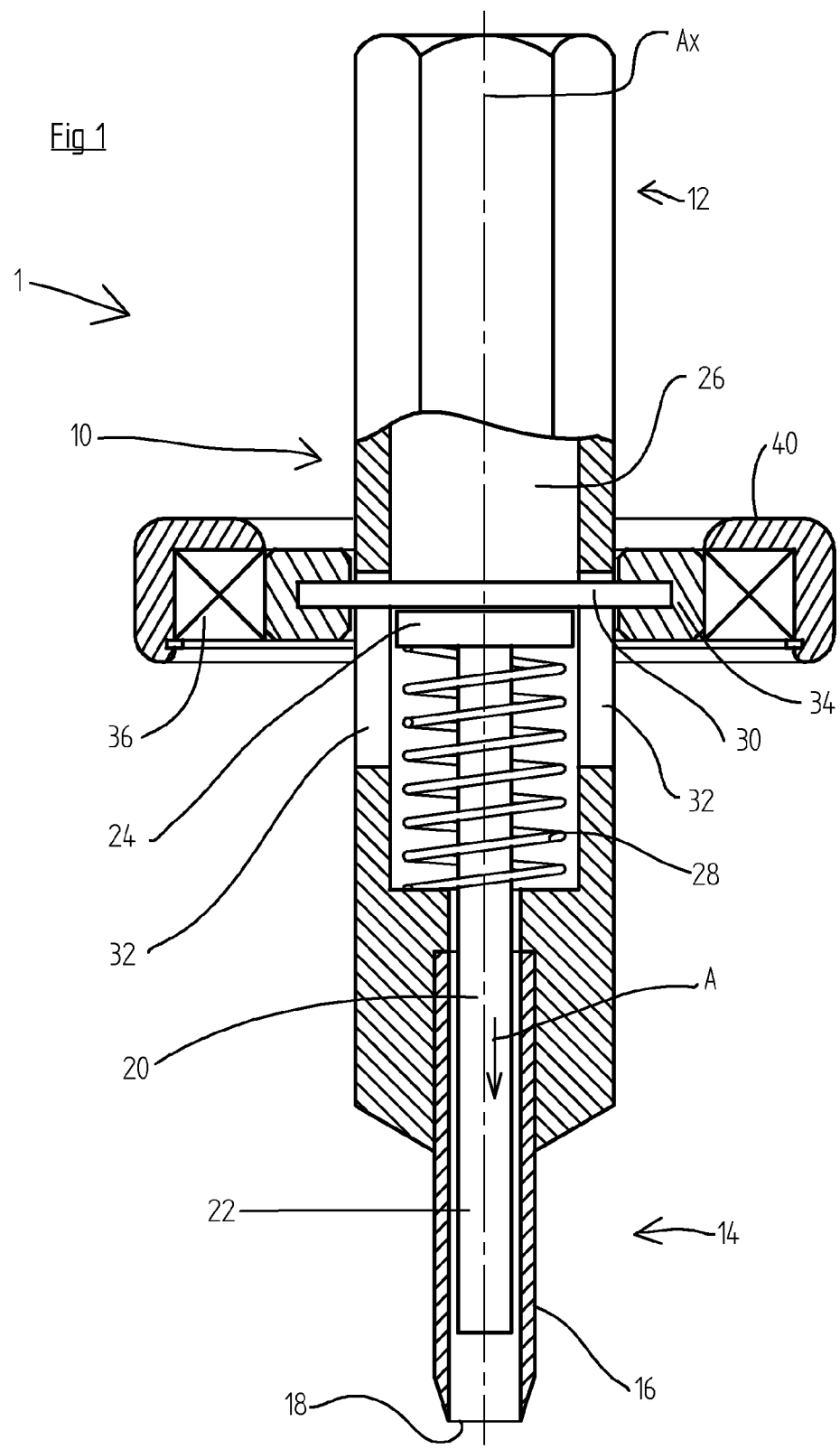

CUTTING TOOLS FOR SAMPLE PREPARATION

CROSS REFERENCE TO RELATED APPLICATIONS

This application claims the priority benefit of PCT/EP2013/067869 filed on Aug. 29, 2013 and Great Britain Application No. 1215504.0 filed on Aug. 31, 2012. The contents of these applications are hereby incorporated by reference in their entirety.

The present invention relates principally to a cutting tool for cutting, handling and then ejecting disks of material cut from a sheet or like material. In particular, but not essentially, the present invention relates to a tool for cutting disks of a sample holding matrix material, such as paper containing a DNA sample, for further analysis.

Prior cutting tools have been proposed which are used for similar purposes to those mentioned above. For example CA2380736, U.S. Pat. No. 5,980,545, and WO2011134040 each show cutting devices with motors, gearing and casings. These devices are expensive to manufacture, and are difficult to maintain or repair, given the complicated mechanisms within each.

Simpler devices exist including a hand held punch having a cutting tip has to be twisted using a wrist action. These tools are simple, but not suitable for continuous use because they require repetitive wrist movement which can be tiresome for the user.

The size of the disks required is generally small, and it is the disk which is of interest to the user. Known tools exist, for example for coring fruit or office paper punches, but these tools produce much larger holes, and the tools are designed to remove and discard the punched core or punched paper.

The inventor has realised that there is a need for an inexpensive sample disk cutting tool which can cut, retain and eject a sample disk of a relatively small size—around 0.5 mm to around 4 mm in diameter in sample holding sheet material or the like.

Thus, according to the invention, there is provided a cutting tool for cutting, handling and then ejecting disks of material cut from a sheet or like material, the tool comprising:

a body having a proximal end adapted to be rotatably driven about an axis, and having a distal end including a generally cylindrical cutting portion rotatable about said axis for cutting and receiving said disks;

an ejector slideable parallel with the axis and within said cylindrical cutting portion for ejecting the received cut disks; and a grip rotatably mounted to the body such that the grip can be held without substantial rotation whilst the body is rotated said grip being operable to cause said sliding of the ejector.

In an embodiment, the body includes a cavity having an opening, and the ejector includes a portion within the cavity which extends away from the axis and through the opening and can slide therein, said portion providing force transmitting communication between the ejector and the grip.

In an embodiment, the portion of the ejector is a pin engageable with the ejector in the cavity and the portion further includes a collar mounted slideably externally of the body, said grip being rotatably mounted to the collar by means of a rolling element bearing or sliding bearing surfaces.

In an embodiment the grip is the outer race of a rolling element bearing or outer section of a sliding bearing.

In an embodiment, the cutting portion of the body is a cutting cylinder formed from the material of the body, or a replaceable part fitted to or into the body.

In an embodiment a resilient element is included in the cavity providing a force to urge the elector toward the proximal end of the body.

In an embodiment, the proximal end of the body includes a hexagonal external formation.

In an embodiment, the grip is an annulus optionally including a handle portion extending away from the axis.

In an embodiment, the body is formed from metal, or a moulded plastics material, for example polypropylene.

The invention extends to a tool according to the first aspect, inserted into a hexagonal receiving aperture of an electrically powered drill or screwdriver and used for cutting and retaining sample disks cut from a sample holding sheet or like material, and for ejecting said cut disks by pushing a stationary grip toward a distal end of the tool.

Figure 2B:
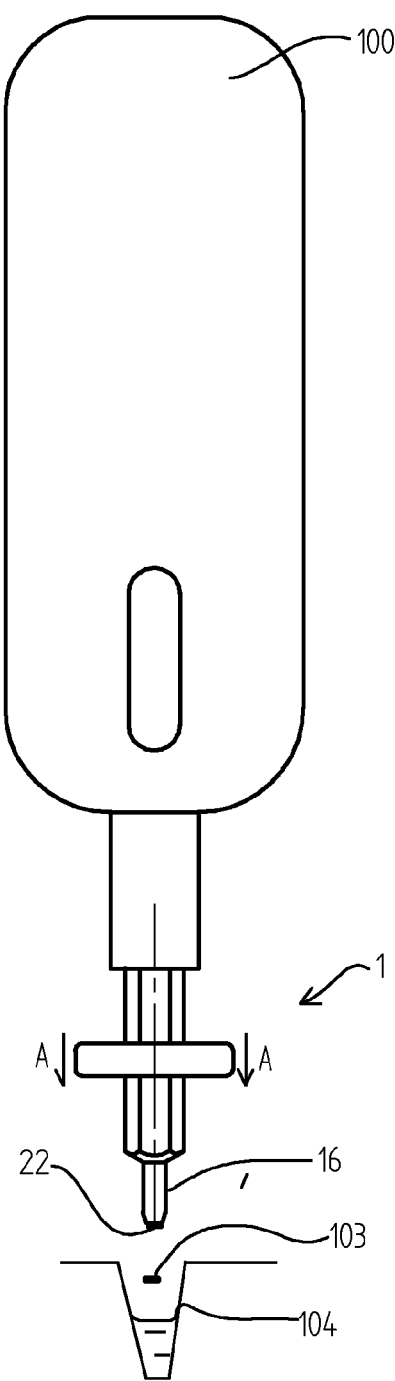

The invention can be put into effect in numerous ways, one example only being described below, with reference to the drawings, wherein:

FIG. 1 shows a partial cross section of a cutting tool; and
FIGS. 2a and 2b show the tool in operation.

Referring to FIG. 1 there is shown a cutting tool 1 having a body 10, shown mostly in section, with its upper, proximal, end 12 shown complete. In this embodiment the proximal end is a hexagonal shank section for fitting to a standard drill or screwdriver for being driven rotatably about an axis Ax.

The body 10 has a distal end 14 which includes a cutting cylinder 16 which has a sharpened cutting tip 18. When rotated, the tip 18 is used to cut small disks from sample holding paper, of the type used for DNA sampling. For example, paper known as FTA and sold by GE Healthcare companies is cut in this way after a DNA containing sample is applied to the paper. Subsequent processing of the disk is used to exact DNA information from the paper.

In use, a disk, once cut, is forced into the cutting cylinder 16 and has to be ejected. For this purpose and ejector 20 is provided. The ejector 20 includes a shaft 22 extending within the cylinder 16 and into a central cavity 26 in the body 10. The ejector has an enlarged head 24. The ejector head 24 is slideable in the cavity, and is urged into the position illustrated, by a resilient member in the form of a spring 28. When the ejector is moved in the direction of arrow A against the force of the spring 28, it is possible to eject any disks which are in the cylinder 16 by pushing them out of cylinder with the ejector shaft 22.

The ejector is moved by means of its engagement with a pin 30 which is slideable in opposed slots 32 formed in the body 10. The pin is connected to an external collar 34 which is also slideable with the pin 30. The collar 34 has a bearing 36 mounted around its periphery, in this case a ball bearing race. The bearing supports a grip portion 40 which in this embodiment is a ring. The grip 40 is can be held by a user and dose not rotate when the body 10 rotates. Thus, the use can push the grip in the direction of arrow A, which will have the effect of ejecting a disk held in the cylinder 16. This can be done whilst the body is still rotating, and so reduces the cycle time for cutting many disks.

FIG. 2a shows the tool 1 mounted to a convention battery screwdriver 100. The tool is rotated and simultaneously pressed against the surface of, for example, FTA paper 101, and a backing mat 102. The result is that a disk of material is forced into the cylinder 16.

FIG. 2b shows the ejected disk 103 and the ejector shaft 22 protruding from the cylinder 16. The disk is, in this case, ejected into a well 104 containing reagents for processing the FTA disk 103, to subsequently obtain DNA information according to known techniques.

The embodiment described above and illustrated is a simple construction which reduces manufacturing costs and is simple and easy to use. The tool can be employed using a standard drill or screwdriver which can rotate at between 10 and 1000 rpm, and preferably about 400 to 600 rpm. Higher speeds have being found to increase static electrical attracting forces which is undesirable because the disk tends to be attracted to the cutting tip 18. Also heat build-up is a problem at higher speeds, which softens or degrades the metal material of the cutting tip 18.

It will be appreciated that additions, modifications, variants, and omissions could be made to the embodiment described and illustrated with departing from the spirit and scope of the invention defined by the claims.

For example, the body is described as hexagonal, but other shapes including a round shape could be employed. It is important that the tool can be attached to a rotatable powered tool, so a hexagonal shank is preferred because that is commonplace, but this attachment could be achieved by use of a conventional three jaw chuck, so a round shank on the tool is possible.

The cutting cylinder 16 is shown as a separate part of the body 10, but the body and cylinder could be made as single piece. It is preferred that the cylinder 16 is a shrink fit into the body 12, such that it is not a replaceable item, but it is possible that the cylinder is replaceably fitted to the body 10, for example by means of a retaining grub screw, or a bayonet or screw fitting. In that case, different size cylinders could be employed providing different diameter disks, using the same body. Although it is envisaged that the cutting cylinder would have a flat tip 18 when viewed in side elevation, a serrated or other shape is possible.

The bearing 36 is preferably a ball race, but, since accuracy of rotation is not important here, any rolling element or plain bearing would suffice. The grip 40 is shown as a separate part to the bearing 36 but, for simplicity, the grip 40 may comprise the out race of said ball race or outer section of another bearing, because it is not essential that the grip be roughened. In fact a smooth surface found on ground bearing surfaces is preferred where higher speeds are used for the tool, because there is then less chance of rubbing a user's fingers when the user tries to stop the already rotating grip portion. A low cost ball race bearing will need little force to stop it rotating, so is preferred for that reason also. The grip could be a plastics or other polymer ring mounted to the bearing and held in place by fiction or an adhesive.

The pin 30 is shown as separate part, could it could be made integral with the ejector 20, for example, as a moulded plastic part. In that case the pin could be made resilient so that it could be assembled in the slots 32, or the slots could be extended to open at the proximal end 12 to aid assembly. The grip 40 may include a handle extending away from the axis Ax.

The invention claimed is:

1. A cutting tool for cutting, handling and then ejecting disks of material cut from a sheet or like material, the tool comprising:
   a body having a proximal end adapted to be rotatably driven about an axis, and having a distal end including a generally cylindrical cutting portion rotatable about said axis for cutting and receiving said disks;
   an ejector slideable axially parallel with respect to the axis and within said cylindrical cutting portion for ejecting the received cut disks, wherein an ejection tip of the ejector is a flat surface;
   a grip rotatably mounted to the body such that the grip can be held without substantial rotation whilst the body is rotated, said grip being operable to cause said sliding of the ejector and for ejecting the disks;
   wherein the body includes a cavity having an opening, and the ejector includes a portion within the cavity which extends away from the axis and through the opening and can slide therein, said portion providing force transmitting communication between the ejector and the grip; and
   wherein a resilient element is included in the cavity providing a force to urge the ejector toward the proximal end of the body.

2. A cutting tool as claimed in claim 1, wherein the portion of the ejector is a pin engageable with the ejector in the cavity and the portion further includes a collar mounted slideably externally of the body, said grip being either rotatably mounted to the collar by means of a rolling element bearing or sliding bearing surfaces, or said grip being formed from an outer race or outer section of said bearing.

3. A cutting tool as claimed in claim 1, wherein the cutting portion of the body is a cutting cylinder either formed from the material of the body, or formed from a separate part.

4. A cutting tool as claimed in claim 1, wherein the proximal end of the body includes a hexagonal external formation.

5. A cutting tool as claimed in claim 1, wherein the grip is an annulus.

6. A cutting tool as claimed in claim 5, wherein the cutting portion of the body is a cutting cylinder formed from a separate part, and wherein the separate part is fitted replaceably to or into the body.

7. A cutting tool as claimed in claim 1, wherein the body is formed from metal, or a moulded plastics material.

8. A cutting tool as claimed in claim 7, wherein the body is formed from polypropylene.

9. A method for operating a tool of claim 1, said method comprising the steps of:
   inserting the tool into a hexagonal receiving aperture of an electrically powered drill or screwdriver;
   rotating the tool when so inserted;
   cutting and retaining a sample disk cut from a sample holding sheet or like material;
   and ejecting said cut disk by pushing a stationary grip on the tool toward the distal end of the tool.

10. The method of claim 9, wherein the portion of the ejector is a pin engageable with the ejector in the cavity and the portion further includes a collar mounted slideably externally of the body, said grip being either rotatably mounted to the collar by means of a rolling element bearing or sliding bearing surfaces, or said grip being formed from an outer race or outer section of said bearing.

11. The method of claim 9, wherein the cutting portion of the body is a cutting cylinder either formed from the material of the body, or formed from a separate part, optionally being fitted replaceably to or into the body.

12. The method of claim 9, wherein the proximal end of the body includes a hexagonal external formation.

13. The method of claim 9, wherein the grip is an annulus optionally including a handle portion extending away from the axis.

14. The method of claim 9, wherein the body is formed from metal, or a moulded plastics material, for example polypropylene.

\* \* \* \* \*